April 23, 1957 T. BRANS Plant Pat. 1,593
CALIFORNIA PRIVET PLANT
Filed Aug. 28, 1956
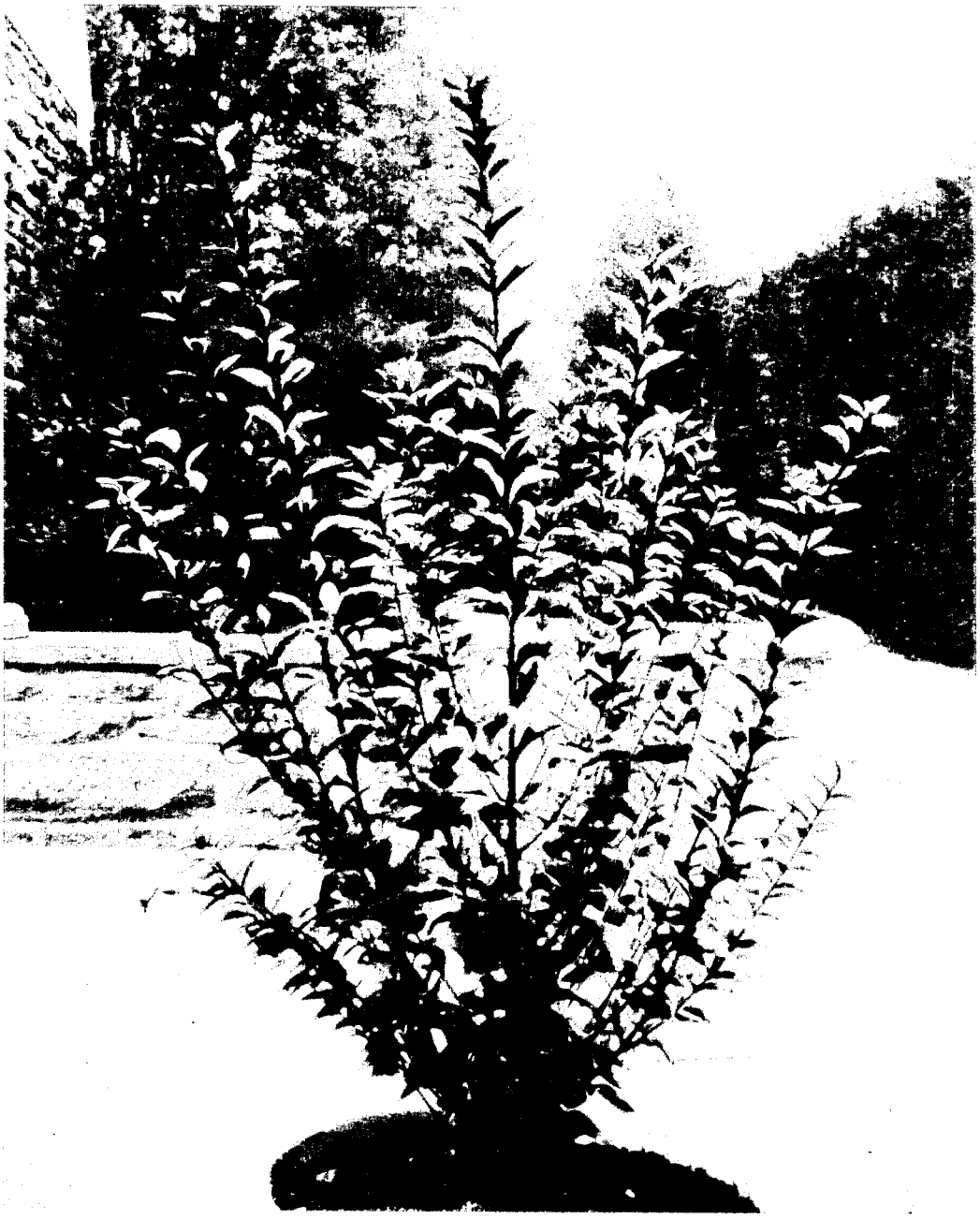
INVENTOR
Theodoor Brans
By Orville M. Kile
Plant Pat. Agt.

United States Patent Office

Plant Pat. 1,593
Patented Apr. 23, 1957

1,593

CALIFORNIA PRIVET PLANT

Theodoor Brans, Boskoop, Netherlands, assignor to Arie D. Vanderkraats, West Grove, Pa.

Application August 28, 1956, Serial No. 606,791

1 Claim. (Cl. 47—59)

My present invention relates to a new, distinct and useful variety of California privet plant, and is a sport of the variety *Aureo-marginatum* (not patented). This sport originated in a block of cultivated privet plants in my nursery at Boskoop, Holland. I reproduced it asexually, by cuttings and by grafts, and developed considerable stock which I observed and tested. It has since been extensively reproduced in the United States by the same means, at West Grove, Pennsylvania, but has not yet been offered for sale to the public. The essential distinctive qualities and characteristics have been well established and transmitted through many generations of asexual reproduction.

My new variety is particularly characterized as to novelty over existing varieties of variegated privet in the following respects:

1. It has a brighter golden, more persistent color tone, with a much higher percentage of golden color areas per plant.

2. The leaves are of somewhat larger size, both as regards length and width, as compared to previously-known golden variegated varieties.

3. The vigor of the plant is markedly superior to that of any other golden variegated variety. In comparison with plants of the parent species of *Ligustrum ovalifolium* grown under the same cultural conditions, the height of my new variety is about twelve inches less at the end of a growing season but it will have many more branches and have a much more bushy appearance, which makes it particularly desirable for cut foliage purposes.

4. In ability to withstand cold weather this new variety is especially noteworthy. After being subjected to prolonged sub-freezing temperatures, as low as eight degrees F. below zero, in West Grove, Pennsylvania, in December 1955, the new variety retained its foliage and color, whereas adjoining plants of the parent variety showed severe injury to their foliage.

The accompanying illustration shows in approximately true color, a plant of my new variety about three years old, from the time it first started to root. The height from the surface of the ground is twenty-six inches.

All technical color references are to the Color Chart of the Royal Horticultural Society; other color references have the usual dictionary meaning.

Somewhat bushy, with many long slender side-branches, the older branches range from light green to brown as the age increases. Terminal branches are yellowish-green in color, approximately matching the basal and nether parts of the adjacent leaves, and giving a harmonious color effect. A high percentage of the leaves, particularly on the newer growth, are entirely golden in color or with only a slight touch of light green along the mid-rib and sometimes along a few of the veins near the base of the leaf. This bright golden color penetrates the leaf structure and is equally visible on the nether side of the leaf, although not so bright in color tone as on the upper side.

On a healthy plant, as the growing season progresses secondary branches develop from the axils of the leaves on the newer wood. These may be two to three inches long and all their leaves—which are small—are bright golden in color, some having slight touches of light green.

*The leaves*

The leaves are located in pairs directly opposite each other and on the newer wood each alternate pair is attached to the branch in a position rotated almost exactly ninety degrees from its neighboring pairs, thus giving the branch approximately the same appearance when viewed from any lateral angle, as in a bouquet.

The leaves on the older part of the new growth, about one foot from the terminal end, will measure at the end of June in the latitude of West Grove, Pennsylvania, about two inches long (including the very short petiole) and about seven-eighths of an inch wide at its widest part. The size decreases of course toward the terminal leaflets.

The leaves on the new growth are rather sharp-pointed, more lanceolate than ovate, and gracefully curved. On the older growth the leaves tend to have a more rounded point—ovate—and to be somewhat shorter in proportion to their length. An average matured leaf will measure approximately 2½ inches long (including the very short petiole) and approximately 1½ inches wide at the broadest point.

Texture: substantial but not heavy.

Veination: parallel, not prominent except for the well-defined midrib.

Color:

*Young foliage.*—Upper surface—Canary Yellow 2/1. In the newest growth, with little or no green, but in many of the leaves a few months old a narrow, uneven strip or blotch of Spinach Green 0926 appears along and adjacent to the midrib. Under surface—Straw Yellow 604, usually with a narrow, uneven strip or blotch of Willow Green 000862/1 along and adjacent to the midrib.

*Mature foliage.*—Upper surface—Lemon Yellow 4/1 usually with a band or splotch of Spinach Green 962 along and adjacent to the midrib. Under Surface—Straw Yellow 604 usually with a band of Willow Green 000862 along and on either side of the midrib.

*The flower*

The flower is of the same general type as other privets but with longer, whiter florets than in many varieties.

Having thus disclosed my discovery, I claim:

The new, distinct and useful variety of golden privet plant, substantially as herein shown and described, characterized particularly by its brighter golden and more extensive coloration, larger leaves, better vigor, and superior hardiness as compared to existing varieties of variegated privet.

No references cited.